United States Patent [19]
Murphy et al.

[11] Patent Number: 5,466,573
[45] Date of Patent: Nov. 14, 1995

[54] PLATELET STORAGE METHOD IN A MEDIUM CONTAINING ACETATE AND PHOSPHATE

[75] Inventors: Scott Murphy, Ardmore, Pa.; Tetsuo Shimizu, Kasugai, Japan

[73] Assignee: Thomas Jefferson University, Philadephia, Pa.

[21] Appl. No.: 286,627

[22] Filed: Aug. 5, 1994

Related U.S. Application Data

[62] Division of Ser. No. 984,272, Dec. 1, 1992, Pat. No. 5,376,524, which is a continuation of Ser. No. 678,699, Apr. 1, 1991, abandoned.

[51] Int. Cl.$^6$ ............................................. A01N 1/02
[52] U.S. Cl. ............................................. 435/2; 424/532
[58] Field of Search ............................ 435/2; 424/532

[56] References Cited

U.S. PATENT DOCUMENTS

| | | | |
|---|---|---|---|
| Re. 32,874 | 2/1989 | Rock et al. | 424/101 |
| 4,390,619 | 6/1993 | Harmening-Pittiglio | 435/2 |
| 4,447,415 | 5/1984 | Rock et al. | 424/101 |
| 4,467,035 | 8/1984 | Harasawa et al. | 435/253 |
| 4,695,460 | 9/1987 | Holme | 424/101 |
| 4,970,143 | 11/1990 | Guidoux et al. | 435/1 |
| 5,043,261 | 8/1991 | Goodrich, Jr. et al. | 435/2 |
| 5,178,884 | 1/1993 | Goodrich, Jr. et al. | 424/533 |
| 5,213,814 | 5/1993 | Goodrich, Jr. et al. | 424/532 |
| 5,328,844 | 7/1994 | Moore . | |

OTHER PUBLICATIONS

Murphy, et al., *Platelet Storage in Synthetic Media Lacking Glucose and Bicarbonate*, Transfusion, vol. 31, No. 1, pp. 16–20, 1991.

Cesar et al., "Plasma Free Fatty Acid Metabolism During Storage of Platelet Concentrates for Transfusion", *Transfusion* 27(5): 434, 437 1987.

Kilkson et al., "Platelet Metabolism During Storage of Platelet Concentrates at 22° C.", *Blood*, 64(2):406–414 1984.

Murphy, "Platelet Transfusion", *Progress in Hemostasis and Thrombosis*, vol. III, Ed. by T. Spaet, Grune and Stratton, Inc. 1976.

Murphy et al., "Platelet storage at 22° C.: Role of Gas Transport Across Plastic Containers in Maintenance of Viability", *Blood* 46(2):209–218 1975.

Murphy et al. "Improved Storage of Platelets for Transfusion in a New Container", *Blood* 60(1):194–200, 1982.

Murphy, "Platelet Storage for Transfusion", *Seminars in Hematology* 22 (3): 165–177, 1985.

Murphy, "The Preparation and Storage of Platelets for Transfusion", Mammon, Barnhart, Lusher, and Walsh, PJD Publications Ltd., Westbury, N.Y., 1980.

Shimizu et al., "Plasma–Poor Platelet Concentrates (PC) Prepared by Autoclave–Sterilized Additive Solution Containing Glucose with Physiological pH", Abstract, presented Nov. 10–15, 1990, meeting of *American Association of Blood Banks*, Los Angeles, California.

Simon, et al. "Extension of Platelet Concentrate Storage", *Transfusion* 23:207–212, 1983.

*ATCC Catalogue of Bacteria and Bacteriophages*, pp. 346, 366, 1989.

*Gibco BRL Catalog*, p. 15, 1990.

Stryer, *Biochemistry*, Third Edition p. 325.

Meryman et al., *Transfusion*, 26, 500–505, 1986.

Wicomb W. et al., Transplantation 49: 261–264 (1990).

*Primary Examiner*—Marian C. Knode
*Assistant Examiner*—S. Saucier
*Attorney, Agent, or Firm*—Woodcock Washburn Kurtz Mackiewicz & Norris

[57] ABSTRACT

The invention is an improved platelet storage method and composition. Medium for the storage of platelets for transfusion comprising acetate or an acetate-like compound and phosphate is disclosed.

17 Claims, 9 Drawing Sheets

PLATELET STORAGE METHOD IN A MEDIUM CONTAINING ACETATE AND PHOSPHATE

This is a divisional of application Ser. No. 07/984,272, filed Dec. 1, 1992, now U.S. Pat. No. 5,376,542, which is a continuation of application Ser. No. 07/678,699, filed Apr. 1, 1991 now abandoned.

BACKGROUND OF THE INVENTION

A great deal is known about human platelet cells. General publications describing techniques, materials, and methods for the storage of platelets are described by Murphy et al. in "Improved Storage of Platelets for Transfusion in a New Container", *Blood* 60(1):194–200 (1982); by Murphy in "The Preparation and Storage of Platelets for Transfusion", Mammon, Barnhart, Lusher, and Walsh, PJD Publications, Ltd., Westbury, N.Y. (1980); by Murphy in "Platelet Transfusion", *Progress in Hemostasis and Thrombosis*, Vol. III, Ed. by T. Spaet, Grune and Stratton, Inc. (1976); by Murphy et al. in "Platelet Storage at 22° C.: Role of Gas Transport Across Plastic Containers in Maintenance of Viability", Blood 46(2):209–218 (1975); by Kilkson, Holme, and Murphy in "Platelet Metabolism During Storage of Platelet Concentrates at 22° C.", *Blood* 64(2):406–414 (1984); by Murphy in "Platelet Storage for Transfusion", *Seminars in Hematology* 22(3): 165–177 (1985); by Simon, Nelson, Carmen, and Murphy in "Extension of Platelet Concentrate Storage", *Transfusion* 23:207–212 (1983); by Cesar, Diminno, Alam, Silver, and Murphy in "Plasma Free Fatty Acid Metabolism During Storage of Platelet Concentrates for Transfusion", Transfusion 27(5):434–437 (1987), each of which publications is hereby incorporated by reference as if more fully set forth herein.

In order to maintain viability, platelets must generate new adenosine triphosphate (ATP) continuously to meet their energy needs. Two chemical pathways are generally available: glycolysis and oxidative phosphorylation. In glycolysis, one molecule of glucose is converted to two molecules of lactic acid generating two molecules of ATP. In oxidation, glucose, fatty acid or amino acid enters the citric acid cycle and is converted to CO2 and water. This pathway requires the presence of an adequate supply of oxygen. It is much more efficient than glycolysis, producing 36 molecules of ATP per molecule of glucose.

It has been recognized that platelets will meet their energy needs in a manner which is not necessarily consistent with their long term storage ex vivo in a viable condition. When given adequate oxygen, platelets produce most of their required ATP through oxidation, but continue to produce lactic acid through glycolysis instead of diverting all metabolized glucose through the oxidative pathway. Therefore, during storage of platelets in plasma, a glucose-containing medium, lactic acid concentrations have been found to rise approximately 2.5 mM per day. This leads to a gradual fall in pH, even in the presence of naturally occurring plasma buffers, principally sodium bicarbonate.

A considerable body of prior art exists concerning storage of platelets. Prior work has shown that the duration of platelet storage is limited by the continuing production of lactic acid by platelets. Although this provides energy for the platelets, the lactic acid produced acidifies the medium containing the platelets, which eventually destroys the cells. It is also known that fatty acids and amino acids may be used as substrates for oxidative metabolism of stored platelet cells.

In routine blood banking practice, platelet concentrates (PC) are prepared by drawing a unit of blood (about 450 ml) into a plastic bag containing an anticoagulant and then centrifuging the blood into three fractions: red cells, plasma, and platelets. The separated platelet fraction is then suspended in approximately 50 ml of plasma. This platelet-containing product is then stored until needed for transfusion into a patient.

A number of interrelated factors have been shown to affect platelet viability and function during storage. For example, the anticoagulant used for blood collection, the method used to prepare PC, and the type of storage container used.

The currently accepted standard practice is to store PC for five days at 22° C.; after five days, it has been shown that platelet function may be impaired. In addition to storage time, other storage conditions have been shown to affect platelet metabolism and function including initial pH, storage temperature, total platelet count, plasma volume, and agitation during storage.

One of the major problems in PC storage is regulation of pH. Virtually all units of PC show a decrease in pH from their initial value of approximately 7.0. This decrease is primarily due to the production of lactic acid by platelet glycolysis and to a lesser extent to accumulation of $CO_2$ from oxidative phosphorylation. As the pH falls, the platelets change shape from discs to spheres. If the pH falls below 6.0, irreversible changes in platelet morphology and physiology render them non-viable after transfusion. An important goal in platelet preservation, therefore, is to prevent this decrease in pH. Platelets must be stored in a container permeable to oxygen since glycolysis is stimulated when oxygen availability is limited.

In association with the decrease in pH, striking deceases in the total amount of ATP per platelet has been observed. It is well known that this reduction of the total ATP level is secondary to the degradation of metabolic ATP to hypoxanthine. The depletion of metabolically available ATP affects platelet function because ATP is essential for such roles in hemostasis as platelet adhesion and platelet aggregation. The ability of PC to maintain total ATP at close to normal levels has been found to be associated with platelet viability.

The composition of platelet storage media has been shown to have a direct effect on the maintenance of platelet function and viability. A number of approaches for the storage of platelets for transfusion have been described.

U.S. Pat. No. 2,786,014 (Tullis) discloses a therapeutic product for injection into humans comprising gelatin, sodium chloride, sodium acetate, carbohydrate (glucose), platelets, and water. It is taught at Col. 2, line 56–62, that the acetate anion acts as an anti-agglutinate for the platelets in this composition. The glucose is disclosed as an example of a hypertonicity-increasing agent.

U.S. Pat. No. Re. 32,874 (Rock et al.) and U.S. Pat. No. 4,447,415 (Rock et al.) disclose a medium for storing platelets in a plasma-free, balanced salt medium. Various additional additives may be added to enhance platelet stability including nutrients, reversible inhibitors of platelet activation, substances to raise cyclic adenosine monophosphate levels, and buffering agents. The disclosed nutrients are fructose, adenine, or acetyl CoA. The reversible inhibitors include indomethacin, quinacrine, or vitamin E. Prostaglandins E1, D2, or I2 are taught for raising AMP levels. The buffering agents disclosed are phosphate or amino acids such as histidine, cysteine, tyrosine, lysine or arginine.

U.S. Pat. No. 4,390,619 (Harmening-Pittiglio) discloses a method of storing and preserving shelf life of platelets for transfusion using ion-exchange resins. These resins provide a source of metabolizing ions in an amount and at a rate sufficient to maintain both pH and ATP levels suitable for transfusion.

While both acetate and phosphate have been used individually in media for storage of platelets for transfusion, the benefits of using them together in a platelet storage medium have not been appreciated previously.

SUMMARY OF THE INVENTION

The invention is concerned with a novel medium for the storage of platelets for transfusion, said medium comprising phosphate and acetate or a ketone body such as acetoacetate, beta-hydroxybutylate, or acetone or a soluble, short-chain fatty acid or other compound which can enter the tricarboxylic acid cycle in a fashion similar to acetate. The medium may also contain standard ingredients such as glucose, sodium, potassium, calcium, magnesium, chloride, citrate, and sulfate.

DETAILED DESCRIPTION OF THE INVENTION

Figure 1:
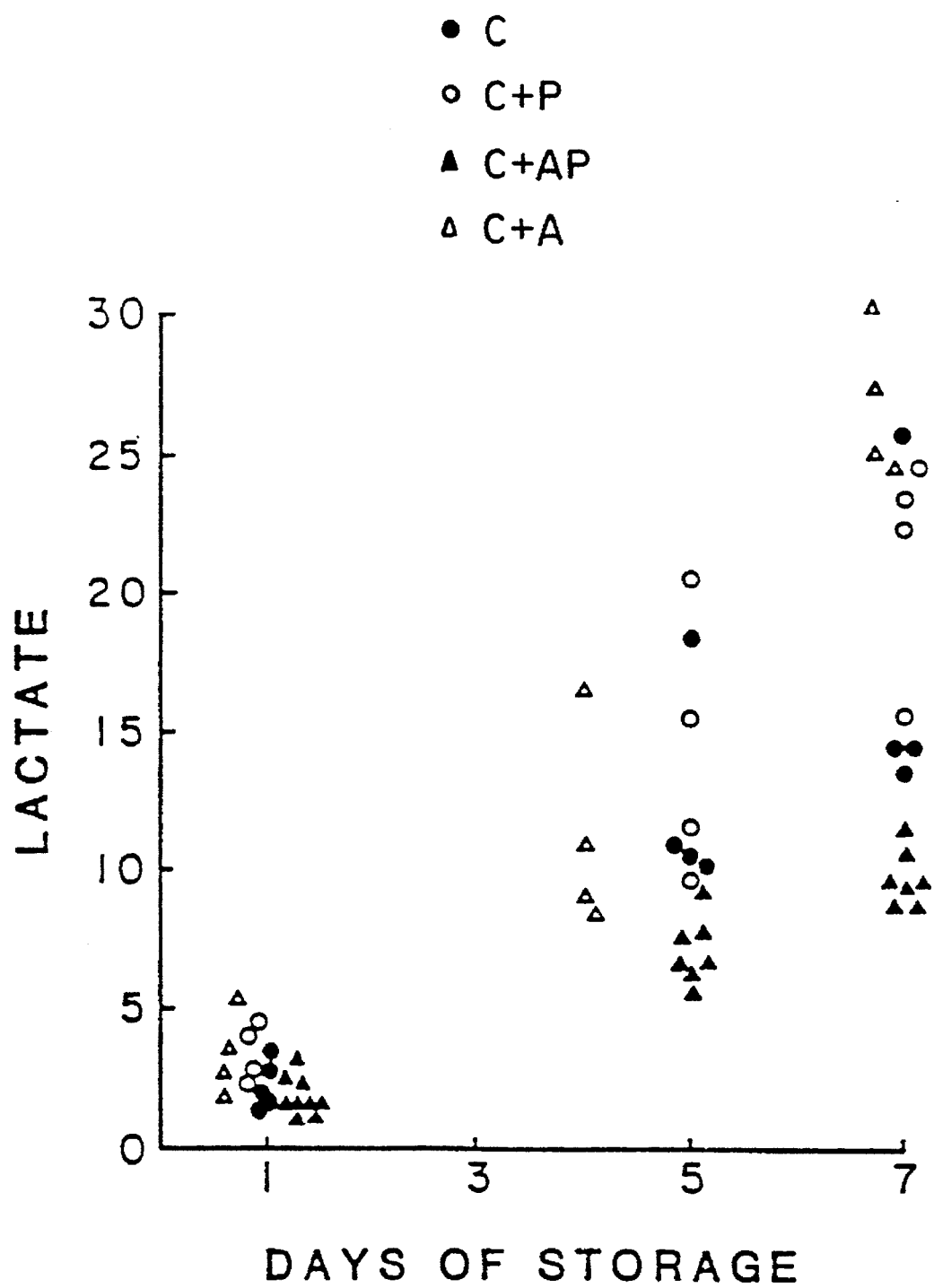
FIG. 1 is a graph showing lactate accumulation over 7 days of storage of platelets in media C, C+P, C+AP and C+A.

This invention relates to a medium for the storage of platelets for transfusion comprising phosphate and substrate for oxidative phosphorylation and for providing buffering upon oxidation. Useful substrates include acetate or a ketone body such as acetoacetate, beta-hydroxybutylate, or acetone or a soluble, short-chain fatty acid or other compound which can enter the tricarboxylic acid cycle in a fashion similar to acetate. Each medium component plays an essential role in maintaining platelet viability. Such acetate, ketone body or soluble, short-chain fatty acid acts as a substrate for oxidative phosphorylation and provides bicarbonate buffer upon oxidation. Phosphate inhibits AMP deaminase, which is activated upon a rise in AMP when acetate or a similar compound reacts with ATP. This is believed to be the basis for the beneficial effect of phosphate when used in combination with acetate, or an acetate-like compound.

The major problems in designing a platelet storage medium have been to include a substrate for oxidative phosphorylation and a buffer to counteract the acidifying effect of the lactic acid which platelets produce during storage. Acetate has been found to be a suitable substrate. In addition, its oxidation produces bicarbonate:

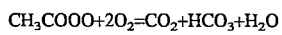

Thus, the use of acetate serves two purposes, i.e., substrate for oxidative phosphorylation and buffer.

However, the initial activation of acetate involves:

The fall in ATP and rise in AMP may activate AMP deaminase leading to depletion of cellular adenine nucleotides which may lead to irreversible cellular damage and acceleration of lactic acid production to compensate for the decrease in ATP. It has been found that phosphate inhibits AMP deaminase, thus preventing this problem in the use of acetate in a platelet storage medium. Phosphate may also act as a buffer and/or provide substrate for resynthesis of ADP and ATP.

While both acetate and phosphate have been used previously individually, the benefits of using them in combination in a platelet storage medium was not appreciated. Platelets stored in the medium of the invention show outstanding in vitro characteristics which correlate with in vivo recovery.

EXAMPLES

Example 1

Preparation of Platelet Storage Medium

In a preferred embodiment, platelet storage medium is prepared as follows. A parent solution identified as "C+AP" is prepared by mixing the following ingredients:

|  | mls |
|---|---|
| Ringers (147.5 mEq/L sodium, 4.5 mEq/L calcium, 4.0 mEq/L potassium, 156 mEq/L chloride) | 270 |
| Sodium Citrate (2.5%) | 80 |
| Dextrose (50%) | 2 |
| KCl (14.9%) | 0.4 |
| MgSO$_4$ (50%) | 0.15 |
| Sodium phosphate (3 mmole/ml) | 2.8 |
| Sodium acetate (2 mEq/ml) | 4.5 |

The resulting solution has an osmolarity of approximately 375, and a pH of approximately 6.5. Approximately 90 ml of water is then added to produce an osmolarity of approximately 300. 1N NaOH is then added to the solution to bring the pH, measured at 22° C., to 7.0 (approximately 2.5 ml).

Example 2

PC were prepared from whole blood donations in accordance with standard methods well known in the art, except that the supernatant plasma was extracted from the bag containing the platelet button as completely as possible using a Fenwal plasma extractor (Fenwal Laboratories, Deerfield, Ill.). Resulting platelet buttons were resuspended in approximately 60 ml of one of three media. Measured concentrations (mM) for each of these media were as follows:

|  | MEDIA | | |
| --- | --- | --- | --- |
|  | C | C + P | C + AP |
| Sodium | 164 | 156 | 167 |
| Potassium | 5.2 | 4.0 | 3.8 |
| Calcium | 1.7 | 1.3 | 1.2 |
| Chloride | 118 | 90 | 88 |
| Magnesium | 0.9 | 0.6 | 0.5 |
| Phosphate | 2.8 | 18.1 | 17.7 |
| Glucose | 15.3 | 12.3 | 10.6 |
| pH | 7.008 | 6.985 | 6.958 |
| Osmolarity | 324 | 310 | 329 |

C, which contains no acetate, is a satisfactory control medium but bicarbonate must be added or pH falls to an unacceptably low level. C+P contains no acetate. Each medium solution was designed to contain the same amount of citrate, i.e., the equivalent of 0.57% sodium citrate. Sodium acetate was added to C+AP to achieve the final concentration, 20 mM. For all figures, the poor results for acetate only addition (C+A) are indicated as triangles for comparison.

Figure 2:
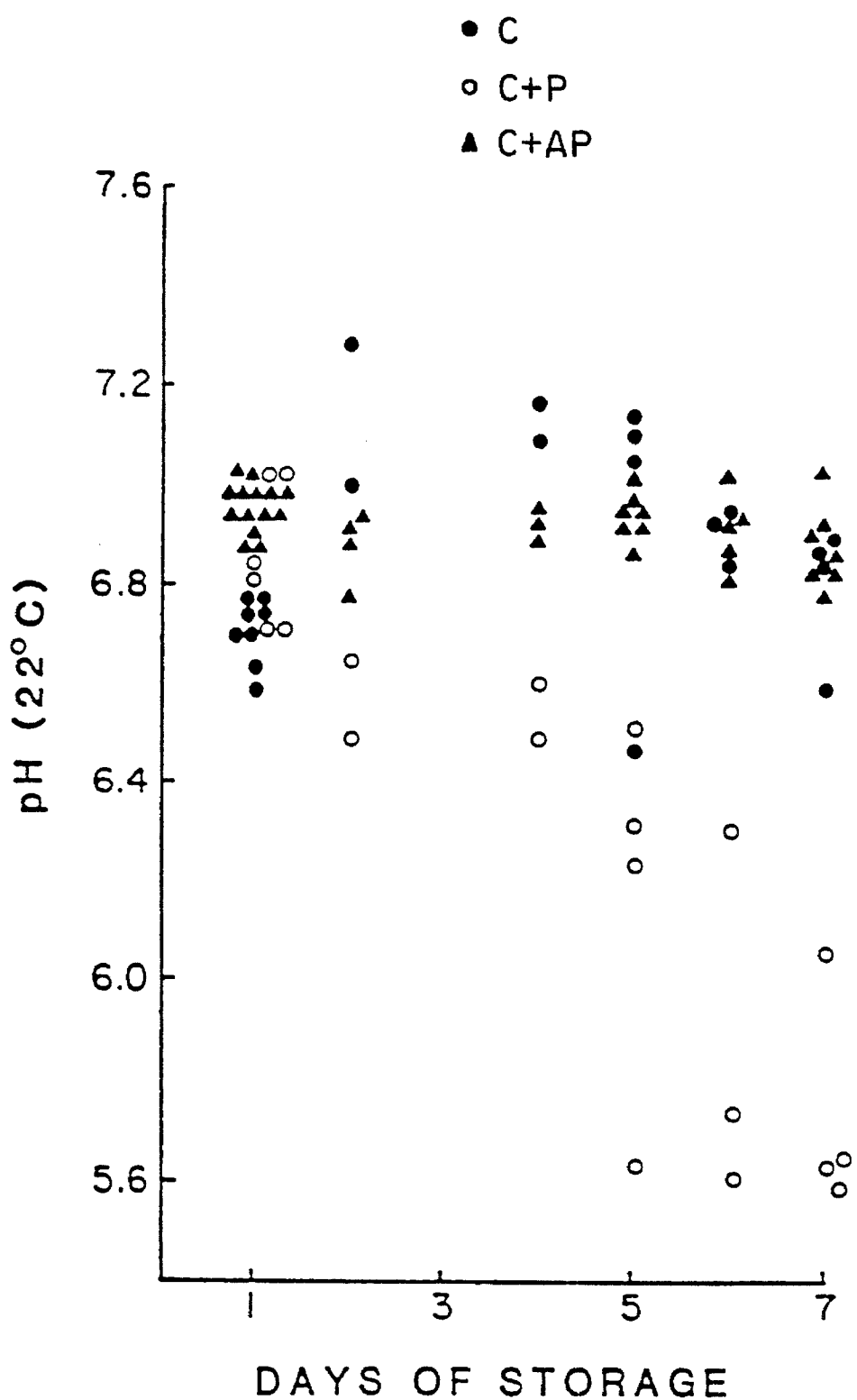
FIG. 2 is a graph showing changes in pH over 7 days of storage of platelets in media C, C+P and C+AP.
Figure 3:
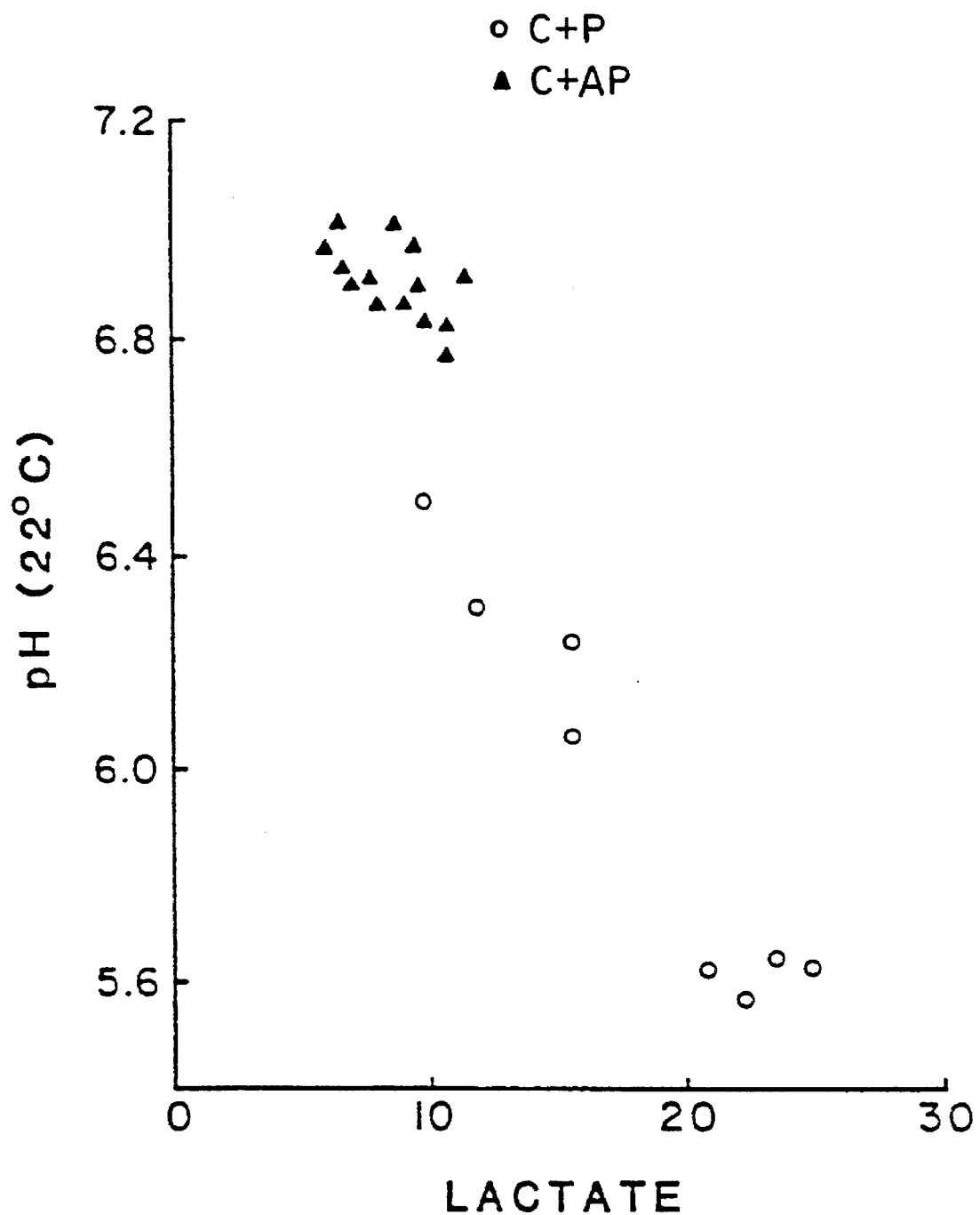
FIG. 3 is a graph showing that superior pH maintenance in C+AP medium is not due simply to reduced rate of production of lactic acid by comparing media C+P and C+AP.

FIG. 1 shows lactate accumulation over 7 days of storage. The slowest lactate rise is seen with C+AP. C has an intermediate position while glycolysis is accelerated in C+P and C+A. FIG. 2 shows pH during storage. It is stable in C because of bicarbonate addition and in C+AP for which bicarbonate addition is unnecessary. However, pH falls to unacceptable levels in C +P. FIG. 3 shows that superior pH maintenance in C+AP is not due simply to reduced rate of production of lactic acid. The relationship between pH and lactate suggests that C+AP provides a buffering effect in spite of the fact that the maximum buffering capacity of acetate is at pH, 4–5.

In these studies, the mean starting PC volume was 64 ml with mean platelet count, $1.4 \times 10^8$. Thus, mean PC platelet content was $9.2 \times 10^{10}$. Daily glucose fall in concentration and rise in lactate concentration were 0.67 mM and 1.28 mM, respectively. Thus, as expected, almost all of the glucose consumption can be accounted for by rise in lactate concentration. Mean bicarbonate concentrations (calculated from pH and $pCO_2$ with the Henderson-Hessalbach equation) were 3.8 and 3.2 meq/liter on days 1 and 7 respectively. Thus, in spite of the continuing accumulation of lactic acid, pH and bicarbonate levels are stable. The best explanation for this derives from the equation for acetate oxidation:

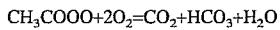

$$CH_3COOO + 2O_2 = CO_2 + HCO_3 + H_2O$$

Thus, a molecule of bicarbonate is produced for every molecule of acetate oxidized.

Figure 4A:
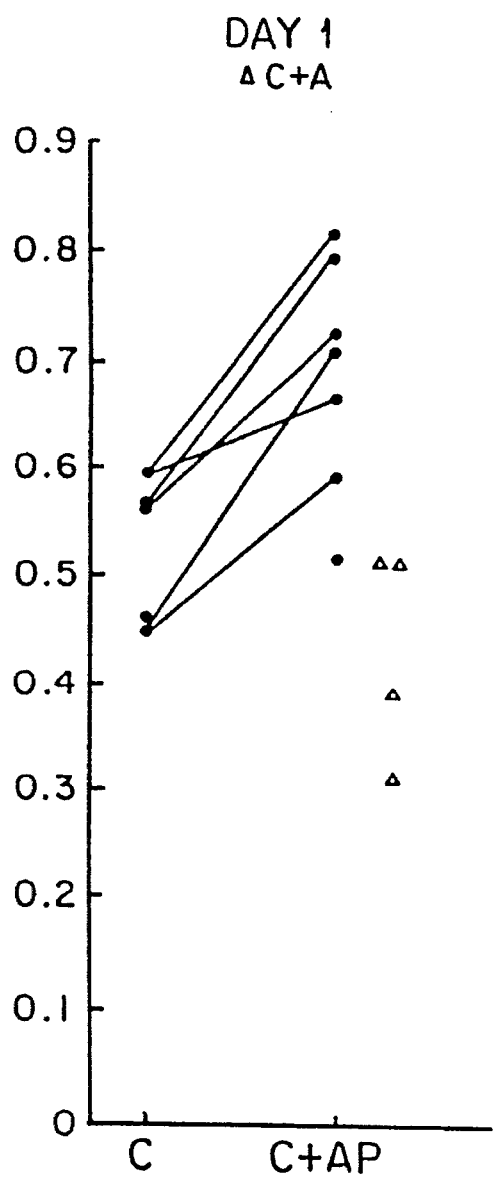
FIG. 4 is a graph showing the rates of oxygen consumption in paired studies in media C and C+AP on day 1 and day 7 of storage. Day 7 is also expressed as a % of day 1. Contrasting results in C+A are shown.
Figure 4B:
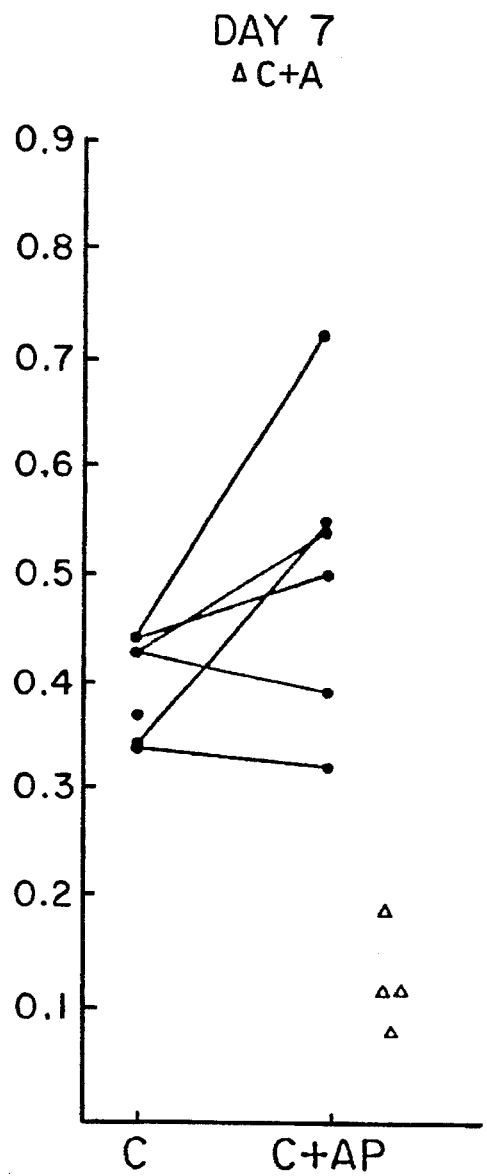
Figure 4C:
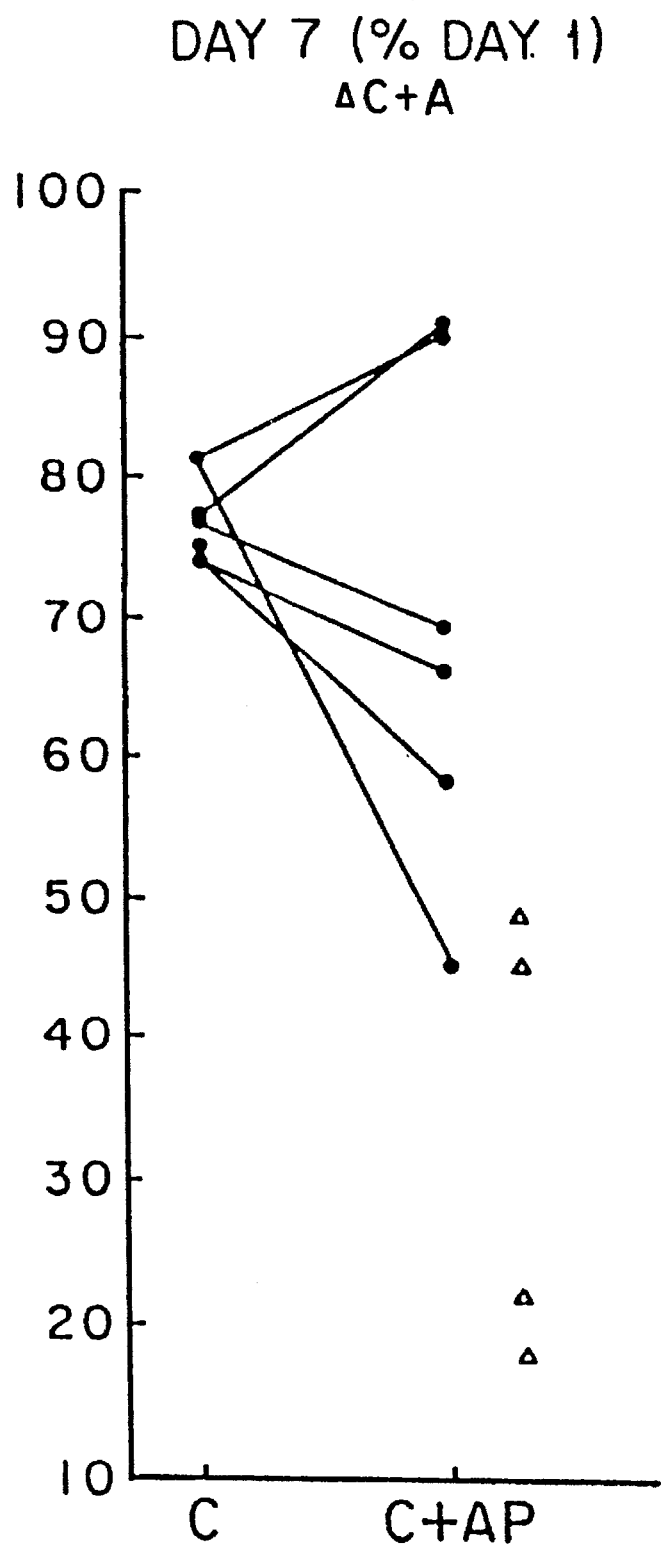
Figure 5A:
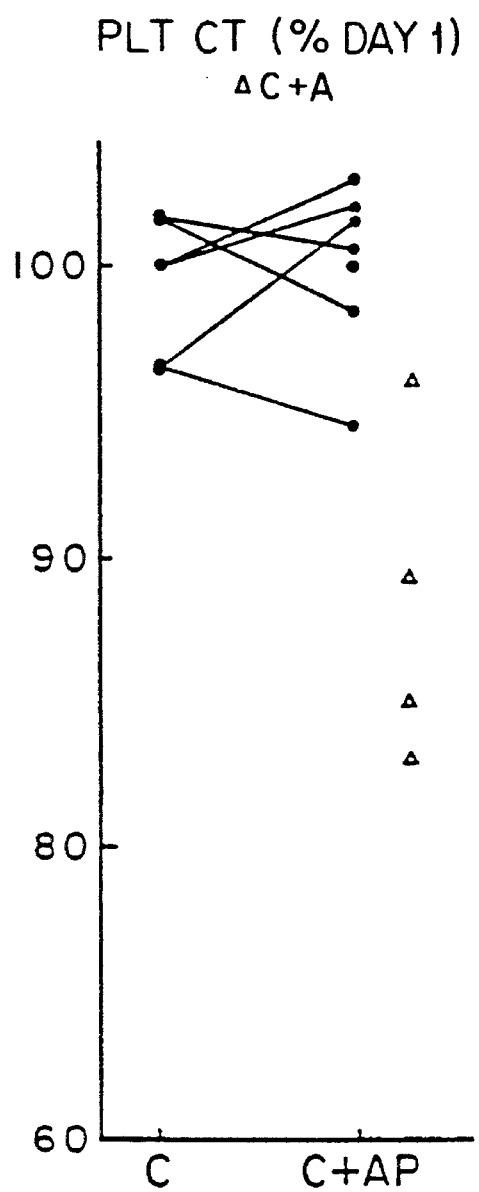
FIG. 5 is a graph showing the platelet count (as % of day 1 plt. count) and % discs, measures of platelet viability, after 7 days of storage in paired studies in media C and C+AP. C+A results are contrasted.
Figure 5B:
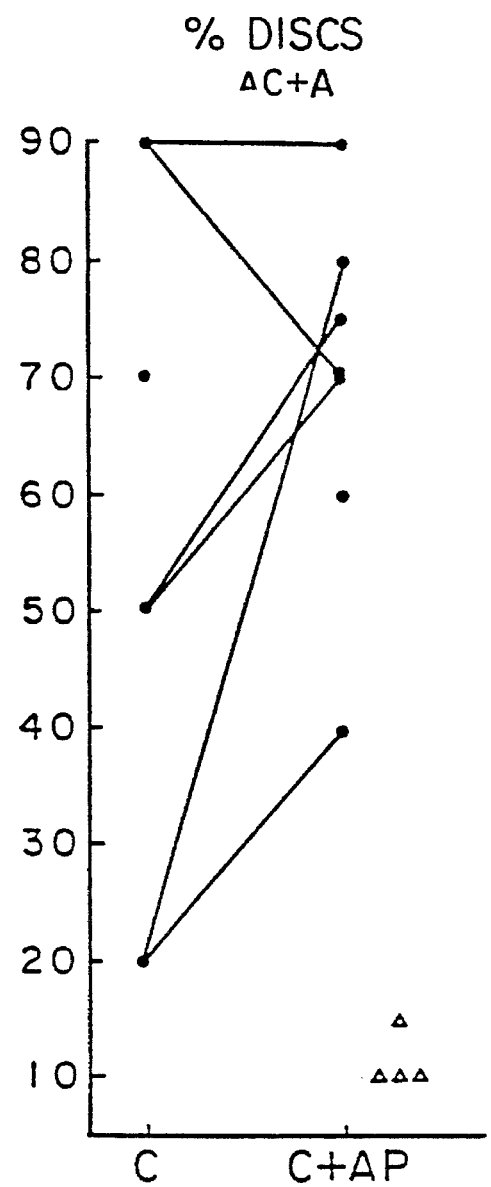
Figure 6A:
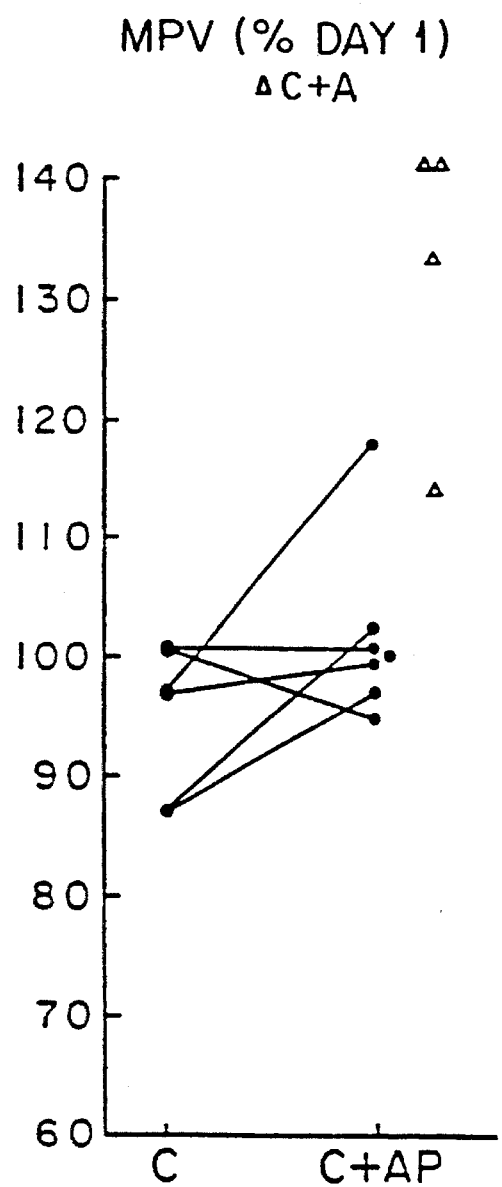
FIG. 6 is a graph showing the mean platelet volume (MPV) (as % of day 1) and dispersion, measures of platelet viability, after 7 days of storage in paired studies in media C and C+AP. C+A results are contrasted.
Figure 6B:
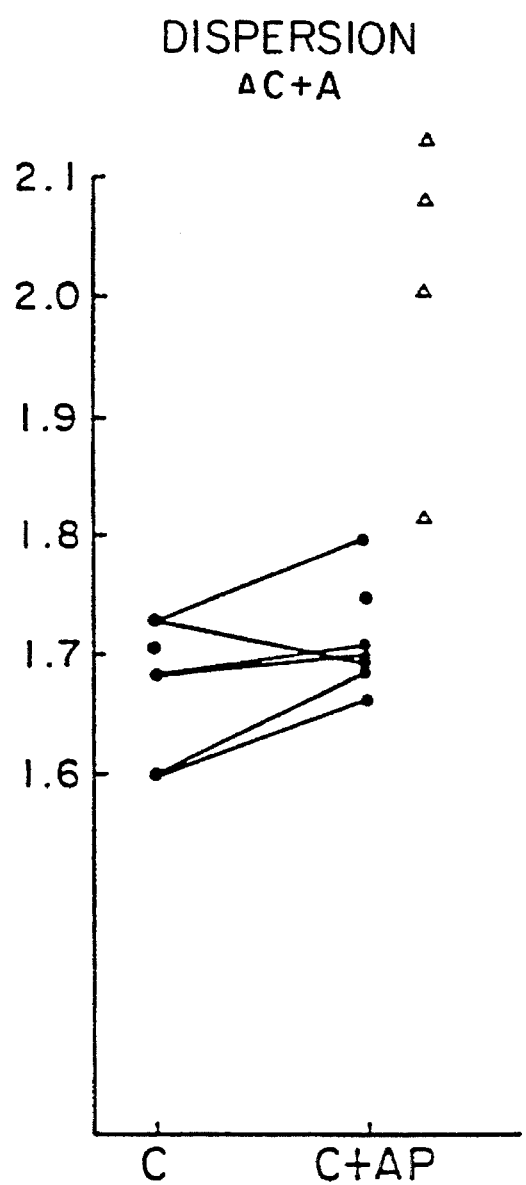
Figure 7A:
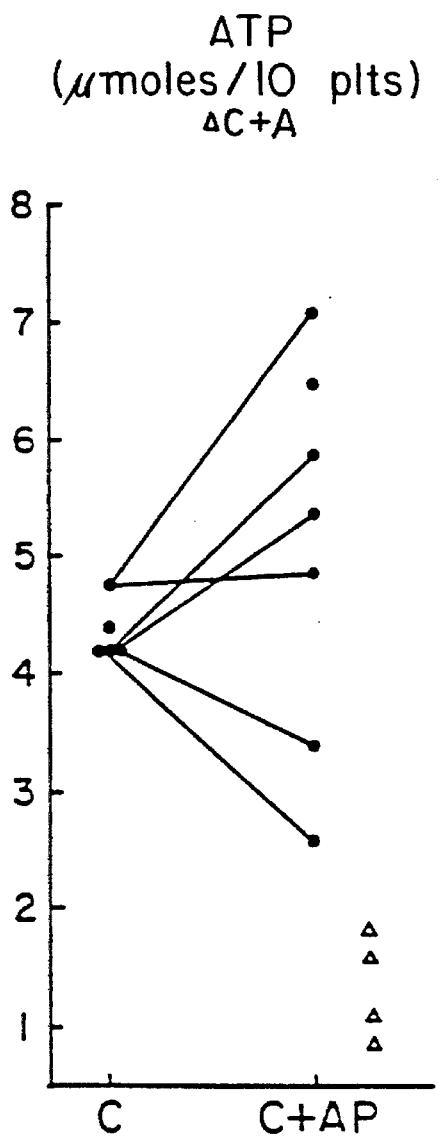
FIG. 7 is a graph showing ATP levels after 7 days of storage in paired studies in media C and C+AP as $\mu m/10^{11}$ platelets and as % of day 1. C+A results are contrasted.
Figure 7B:
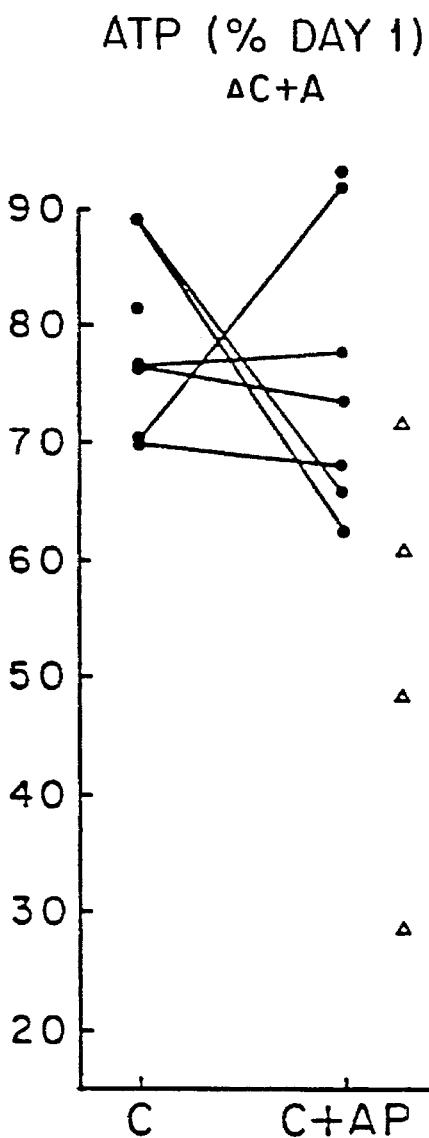
Figure 8A:
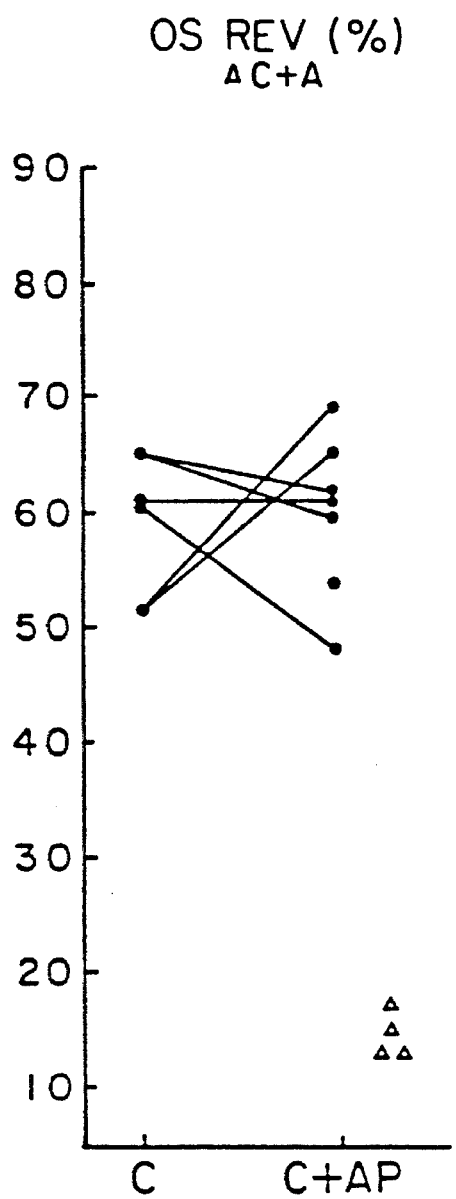
FIG. 8 is a graph showing osmotic reversal reaction (OS REV) (both % and as % of day 1) after 7 days of storage in paired studies in media C and C+AP. C+A results are contrasted.
Figure 8B:
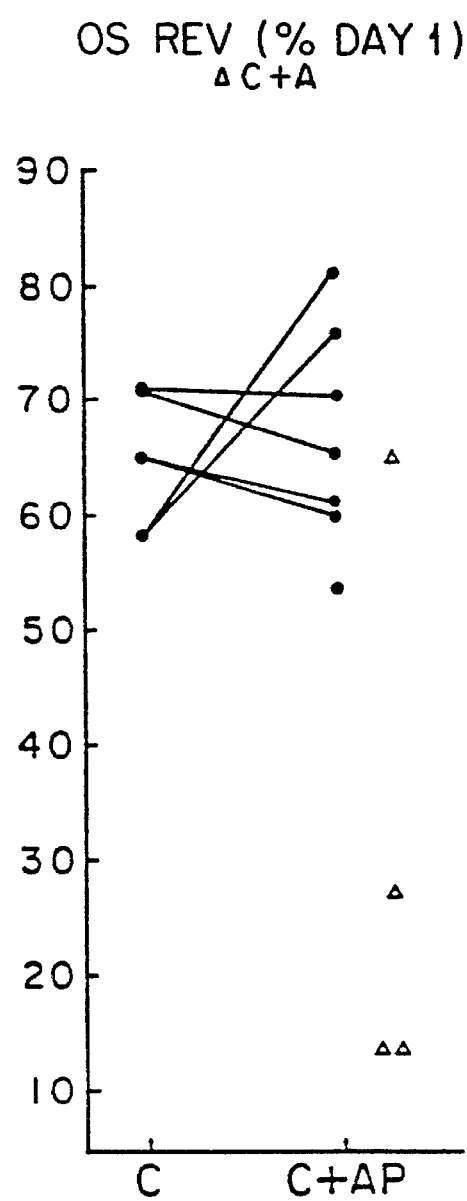

FIG. 4 shows that the rates of oxygen consumption for C+AP are consistently higher than for C by approximately 35% on day 1 of storage. This higher oxygen consumption persists on day 7. The oxygen consumption data translates into approximately 2.2 mmoles oxygen consumed per day per liter of PC. If all oxygen consumption were devoted to acetate oxidation, this would result in a fall in acetate concentration of approximately 1 mM per day and the generation of 1.1 mM bicarbonate per day. This essentially accounts for the buffering of the lactic acid being produced without consumption of the bicarbonate provided by plasma carryover. In the next series of experiments in the lab, we will measure acetate concentrations during storage. The results do suggest that 10 mM acetate should be satisfactory in an ideal PSM.

FIGS. 5–8 present results on day 7 of storage of in vitro laboratory measurements which have correlated with in vivo viability in the past. These include plt ct (platelet count as a % of day 1), % discs (by oil phase microscopy), MPV (mean platelet volume as a % of day 1), dispersion of the Coulter size distribution, ATP (both as an absolute number and as a % of day 1), and os rev (osmotic reversal reaction both as an absolute number and as a % of day 1).

The medium for storage of platelets for transfusion of the present invention, therefore, offers significant advantages over prior art media.

What is claimed is:

1. A method for storing platelets in an essentially plasma-free aqueous medium for subsequent intravenous transfusion to humans, consisting essentially of:
    (a) adding human blood platelets to said medium to form a platelet concentrate, said medium comprising
        (1) a sugar, capable of promoting the formation of adenosine triphosphate, consisting of glucose;
        (2) 3–20 mM phosphate; and
        (3) 3–20 mM acetate as a substrate for oxidative phosphorylation and for providing buffering upon oxidation;
    wherein the pH of said medium is from about 6.8–7.2; and
    (b) storing said platelets in said medium as said platelet concentrate for at least one day.

2. The method of claim 1 wherein the phosphate is present in a concentration of from 8.4 to 20 mM in said medium.

3. The method of claim 1 wherein the osmolarity of said medium is less than 350 milliOsm.

4. The method of claim 1 wherein said medium further comprises at least one additive selected from the group consisting of sodium, chloride, calcium, potassium, citrate, magnesium, and sulfate.

5. The method of claim 1 wherein the pH of said platelet concentrate is maintained at a level above 6.8 during said storage.

6. The method of claim 5 wherein said platelets are stored in said medium for at least 5 days.

7. A method for storing platelets in an essentially plasma-free aqueous medium for subsequent intravenous transfusion to humans, consisting essentially of:
    (a) adding human blood platelets to said medium to form a platelet concentrate, said medium consisting essentially of
        (1) a sugar, capable of promoting the formation of adenosine triphosphate, consisting of glucose;
        (2) 3–20 mM phosphate;
        (3) 3–20 mM acetate as a substrate for oxidative phosphorylation and for providing buffering upon oxidation; and
        (4) an aqueous electrolyte solution in which the sugar, phosphate, and acetate are dissolved, wherein the pH of the medium is from about 6.8–7.2; and
    (b) storing said platelets in said medium as said platelet concentrate for at least one day.

8. The method of claim 7 wherein the phosphate is present in a concentration of from 8.4 to 20 mM in said medium.

9. The method of claim 7 wherein the osmolarity of said medium is less than 350 milliOsm.

10. The method of claim 7 wherein the pH of said platelet concentrate is maintained at a level above 6.8 during said storage.

11. The method of claim 10 wherein said platelets are stored in said medium for at least 5 days.

12. A method for storing platelets in an essentially plasma-free aqueous medium for subsequent intravenous transfusion consisting essentially of
   (a) adding human blood platelets to said medium to form a platelet concentrate, said medium consisting of
      (1) glucose;
      (2) 3–20 mM phosphate;
      (3) 3–20 mM acetate as a substrate for oxidative phosphorylation and for providing buffering upon oxidation; and
      (4) an aqueous electrolyte solution comprising at least one additive selected from the group consisting of sodium, chloride, calcium, potassium, citrate, magnesium, and sulfate, wherein the pH of said medium is from about 6.8–7.2; and
   (b) storing said platelets in said medium as said platelet concentrate for at least one day.

13. The method of claim 12 wherein the acetate is present in an amount of 10 mM in said medium.

14. The method of claim 12 wherein the phosphate is present in a concentration of from 8.4 to 20 mM in said medium.

15. The method of claim 12 wherein the osmolarity of said medium is less than 350 milliOsm.

16. The method of claim 12 wherein the pH of said platelet concentrate is maintained at a level above 6.8 during said storage.

17. The method of claim 12 wherein said platelets are stored in said medium for at least 5 days.

* * * * *